US00PP09787P

United States Patent [19]

Otani

[11] Patent Number: Plant 9,787

[45] Date of Patent: Jan. 28, 1997

[54] CHERRY TREE: 'RED CRYSTAL'

[75] Inventor: Hideki Otani, Reedley, Calif.

[73] Assignee: Otani Enterprises, Reedley, Calif.

[21] Appl. No.: 370,578

[22] Filed: Dec. 19, 1994

[51] Int. Cl.[6] ..... A01H 5/00

[52] U.S. Cl. ..... Plt./37

[58] Field of Search ..... Plt./37

[56] References Cited

U.S. PATENT DOCUMENTS

P.P. 6,676 3/1989 Hansche ..... Plt./37

*Primary Examiner*—James R. Feyrer

*Attorney, Agent, or Firm*—Staas & Halsey

[57] ABSTRACT

A new variety of cherry tree is disclosed characterized by an earlier maturing, dark red colored, sweet cherry fruit than Brooks.

6 Drawing Sheets

BACKGROUND OF THE INVENTION

The present invention relates to a new and distinct variety of cherry tree given the denomination RED CRYSTAL.

The primary, distinctive features of this new variety over existing varieties are early maturing, dark red color, and sweet cherry fruit.

SUMMARY OF THE INVENTION

This new variety is characterized by a very early maturing, dark red colored, sweet cherry.

In the following plant description, color definitions are from "Dictionary of Color" by Maerz and Paul, 1st edition published in 1930.

BRIEF DESCRIPTION OF THE VARIOUS FIGURES OF THE DRAWINGS

DETAILED BOTANICAL DESCRIPTION OF THE CLAIMED TREE

Figure 1:
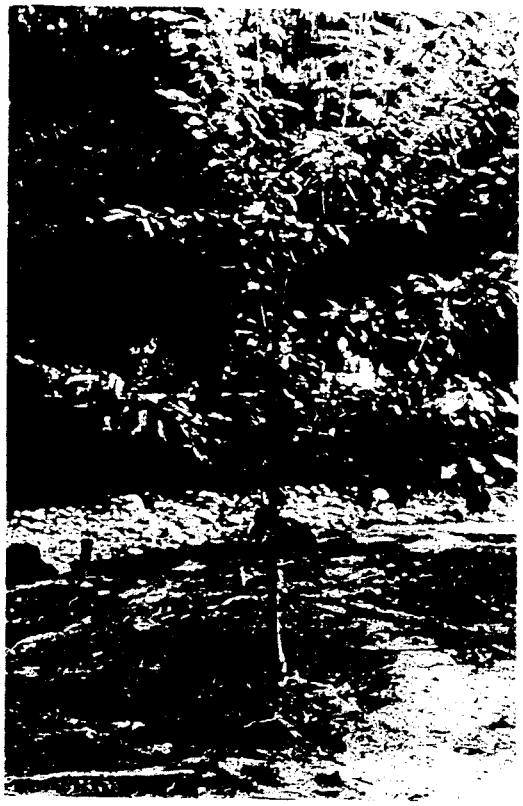
FIG. 1 illustrates the tree of the new variety produced by asexual grafting.
Figure 2:
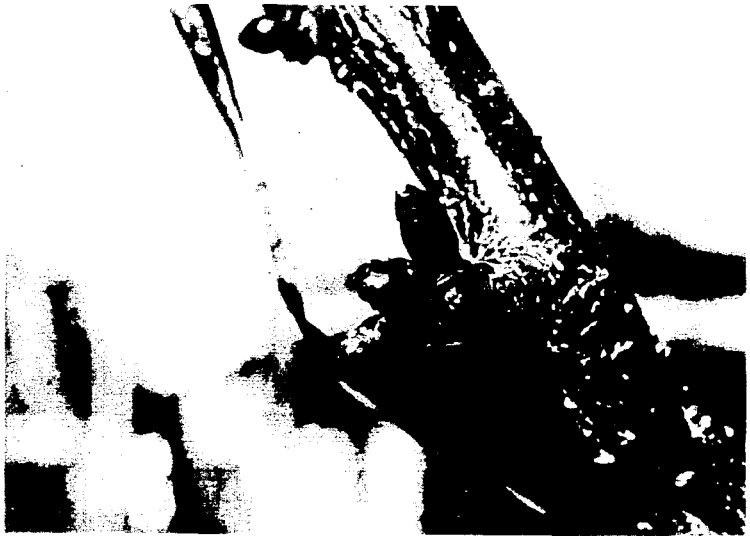
FIG. 2 illustrates a cluster of buds formed on the tree of the new variety.
Figure 3:
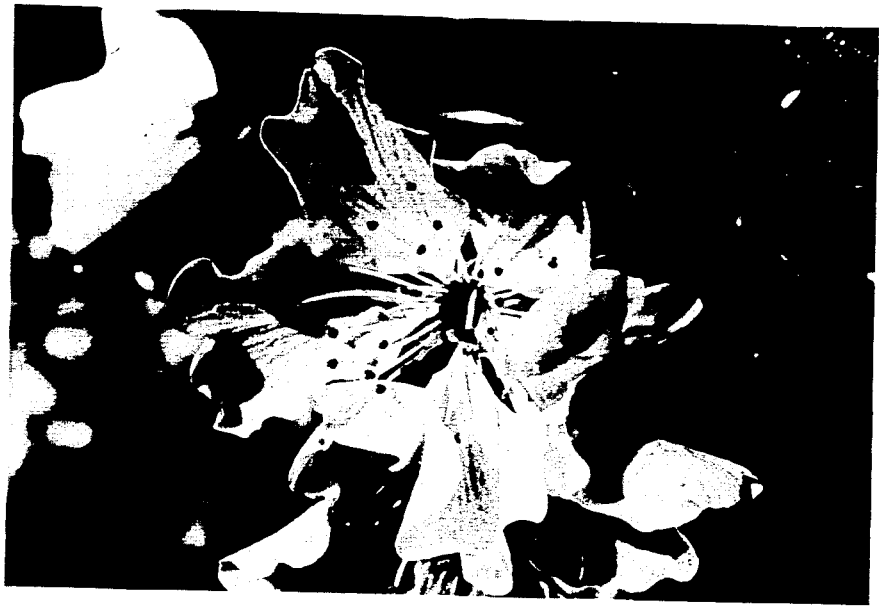
FIG. 3 illustrates flowers on the tree of the new variety on Mar. 23, 1994.
Figure 4:
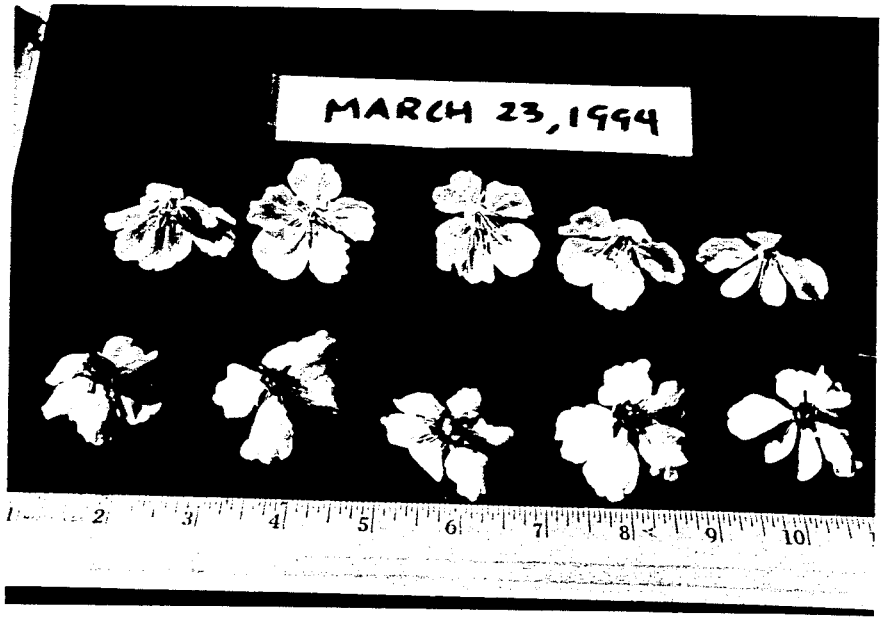
FIG. 4 illustrates flowers of the new variety on Mar. 23, 1994.
Figure 5:
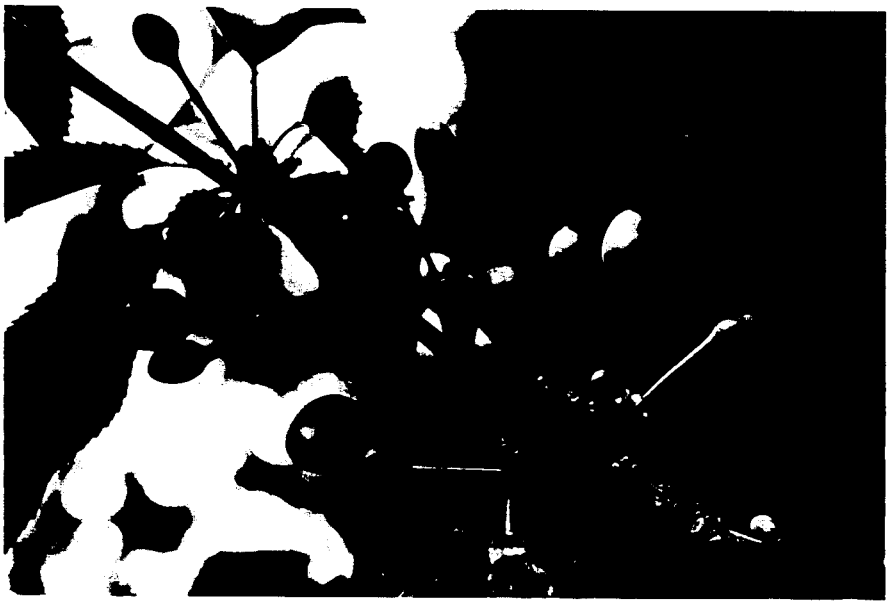
FIG. 5 illustrates early stage fruit growth on the tree of the new variety on Apr. 9, 1994.
Figure 6:
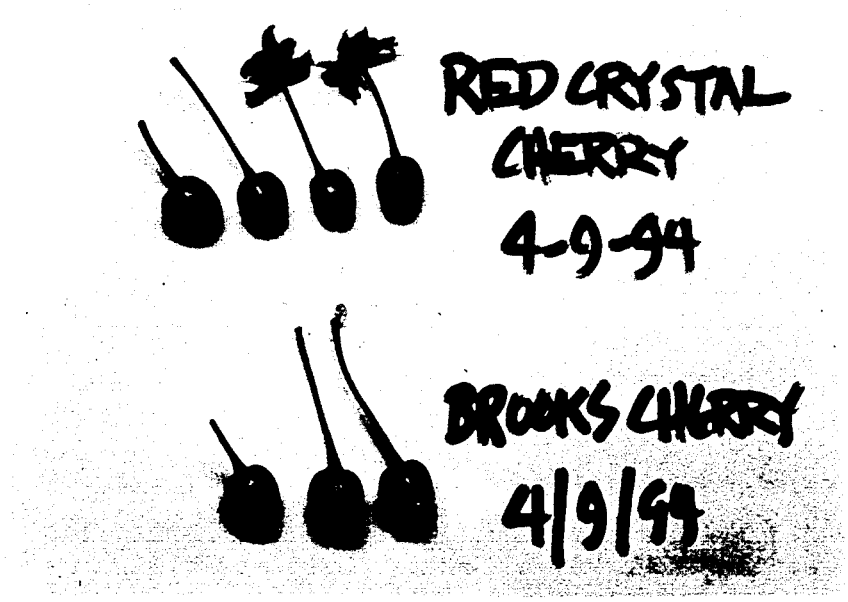
FIG. 6 illustrates early stage fruit growth of the new variety on Apr. 9, 1994, compared with Brooks variety of cherry picked on the same day.
Figure 7:
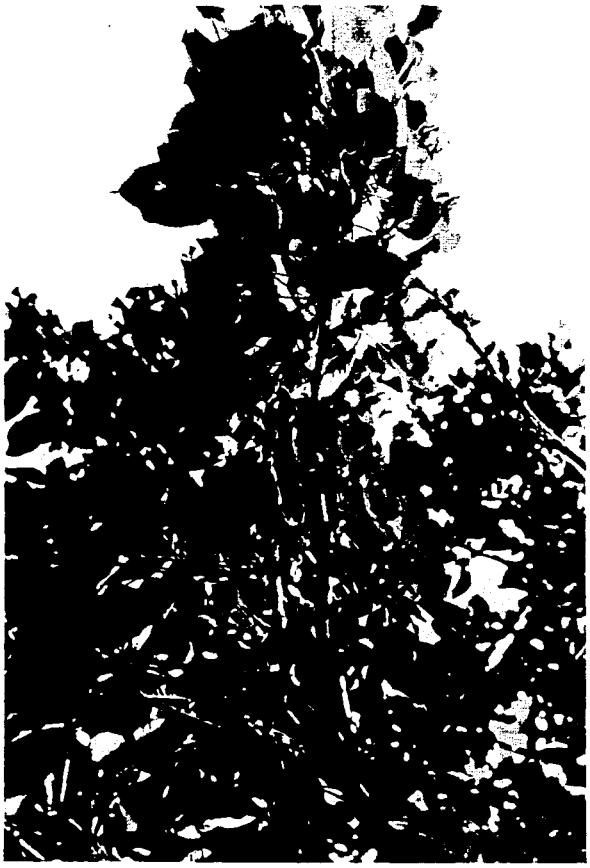
FIG. 7 illustrates medium stage fruit growth on the tree of the new variety on Apr. 16, 1994.
Figure 8:
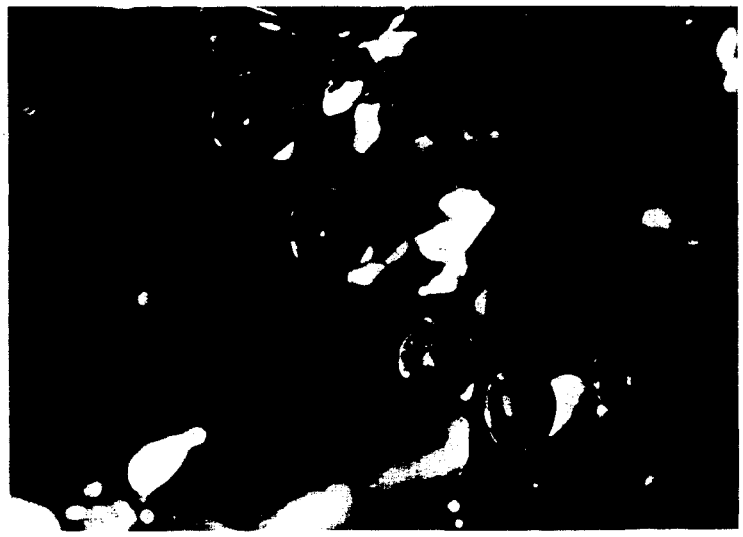
FIG. 8 illustrates fruit of the new variety on the tree on Apr. 20, 1994, compared with fruit of the Brooks variety picked on the same day.
Figure 9:
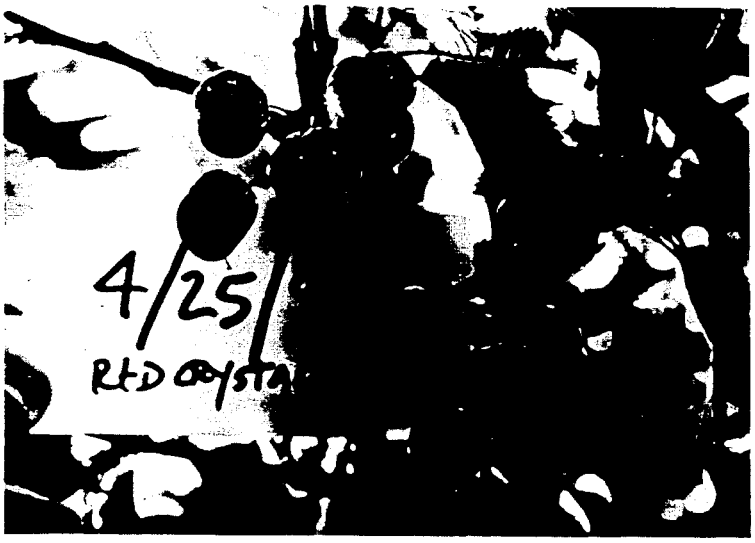
FIG. 9 illustrates a cluster of ripe fruit of the new variety on the tree on Apr. 25, 1994.
Figure 10:
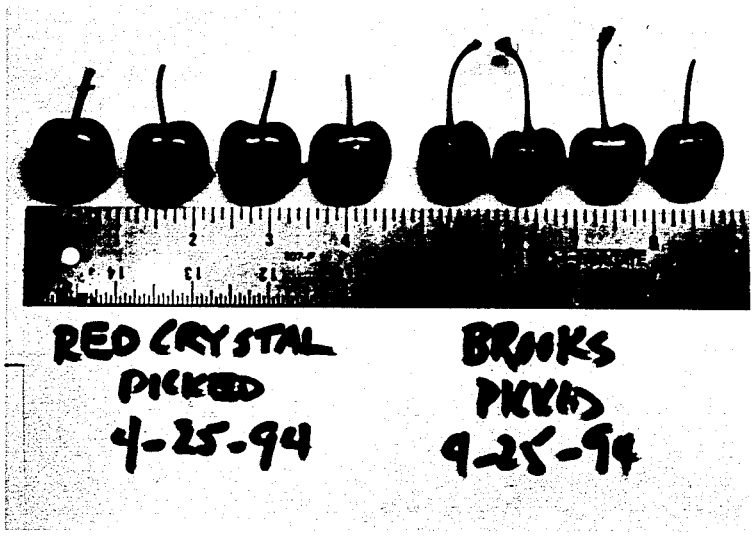
FIG. 10 illustrates fruit of the new variety picked on Apr. 25, 1994, compared with fruit of the Brooks variety picked on the same day.
Figure 11:
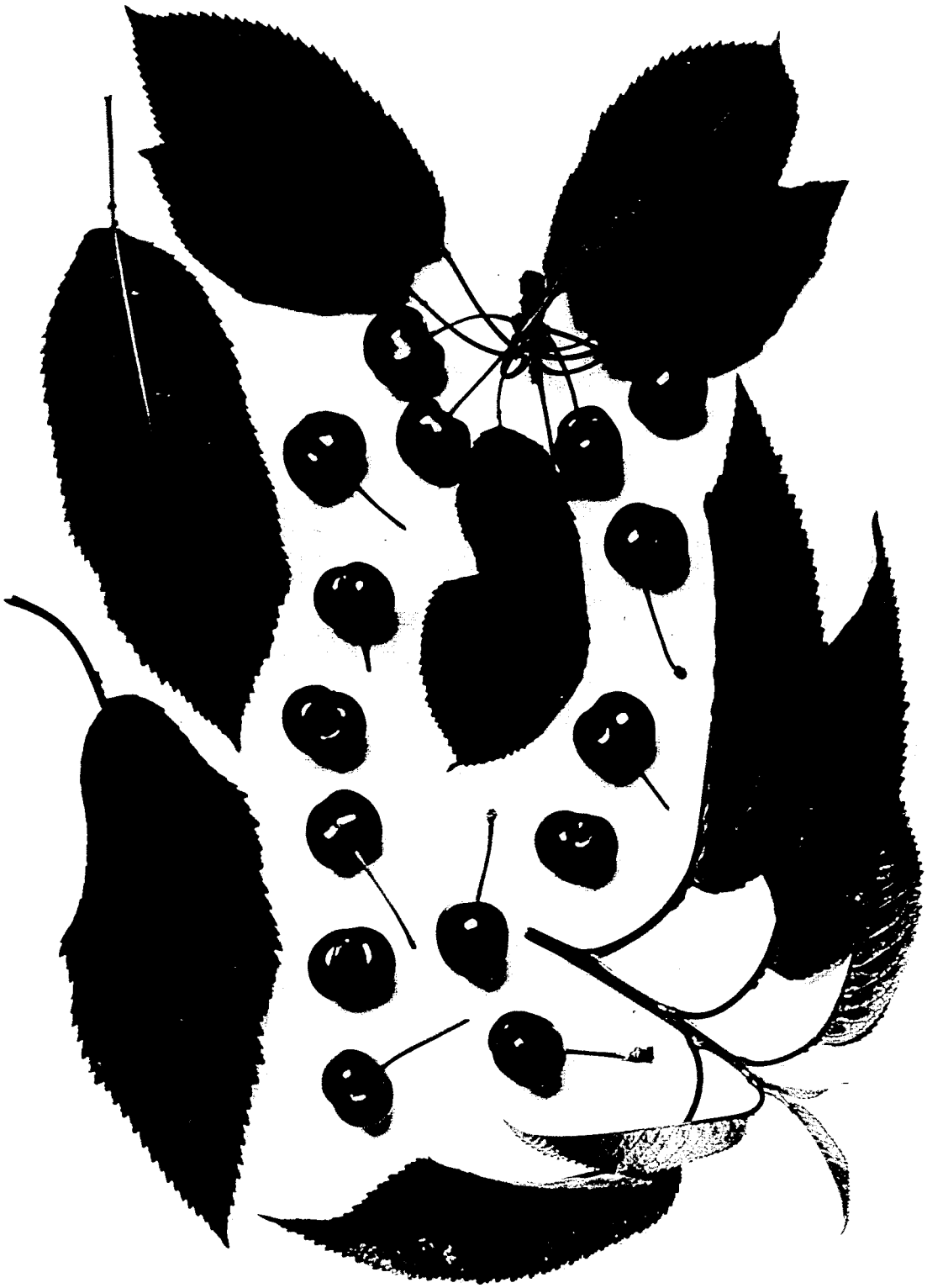
FIG. 11 illustrates fruit, stems and leaves which are typical of the new variety.

A. Genus and species: *Prunus avium L.*

B. Name: 'Red Crystal'.

C. Type/market class: Sweet Cherry Tree.

D. Characteristics:

1. *Tree.*—The tree that resulted from asexual reproduction is vigorous in growth and from upright to upright-spreading in form. The tree is trained in an open vase type of training system. Tree spread is approximately 12 feet in width. Tree height attained in 1994 is from 15 to 16 feet with from 2.5 to 3.5 feet of that height developed as new extension growth during the 1994 growing season. The tree is hardy under typical Central San Joaquin Valley climatic conditions and produces fruit on a regular basis. The vigor is medium. The measured length of terminal growth before it turns to wood (brown) is about 2½ feet to the vertical tip of a three year old tree located at N.W. Sellers and Sunset Avenue, Brentwood, Calif.
2. *Trunk.*—The trunk is of medium thickness, with a trunk circumference of 30 inches at a height of 2 feet above ground level. The trunk bark is of medium texture with a slight amount of grey scarfskin present over the surface. Numerous moderately large bark lenticels are present. These lenticels are generally oval in form and flattened horizontally. The lenticels range from 3.5 to 9.5 mm in width and from 1.0 to 2.5 mm in height. Mature bark color is a brown-grey (8-H-8 Cordovan Brown).
3. *Branches.*—The new variety does not prolifically branch with the branches spreading. Well spaced scaffold branches attach to the main stem at angles of about 80 degrees. Fruit grows in spur-type habit with short internodes. Very minimal pruning is required.

Two year or older wood is medium in thickness and moderately smooth, but often with small, oval and slightly raised lenticels present. These lenticels range from 1.0 to 1.5 mm in width and average 1.0 mm in height. Current season's shoots are relatively smooth and essentially glabrous in surface texture. Color of two year or older branches vary from a grey-brown (7-C-8 Mauve Taupe) to a medium brown (7-E-11 Trotteur Tan). The color of the current season's shoots is a light green (20-L-3 Certosa Green). Internode length on current season's growth is variable, from 14 to 24 mm between nodes on fruiting hangar wood. The shorter internode measurements are usually present in the basal area of the shoot. Leaves on the new expanding shoot tips are a rust-green color (15-A-10 English Oak), and the newest (distil) portion of the shoot itself is often tinged a bronze-green color (15-L-10 Antique Bronze). Thinning is not required for fruit of this new variety to attain disclosed size. Good uniformity of medium to large sized fruit attainable without thinning.

4. *Leaves.*—Leaves are generally large in size. Leaf measurements are taken from leaves growing on vigorous, upright, current season's shoots. Leaf length ranges from 13.3 to 15.9 cm. This is a measurement of the leaf blade only and does not include the petiole. Leaf width varies from 5.9 to 7.6 cm. Leaf thickness is normal. Form: Leaf form is most frequently lanceolate. Leaf tip form is acute to at times acuminate. At other times, however, the leaf apex form appears somewhat dentate, and the apex is slightly twisted sideways. Color:

The leaf upper surface is deep green in color (24-L3) with a gloss surface. The lower leaf surface a lighter grey-green (22-J-5 Leek Green), with a somewhat more dull surface finish. Margins:

Margin form is variable but most frequently serrate with some irregularity in the size of the serrations. Both large and small serrations are commonly present. The leaf surface is nearly flat with only a slight marginal undulation. Petiole:

The leaf petiole is large in size, from 44 to 55 mm in length and from 1.5 to 2.0 mm in thickness. The petiole is pale green in color on the lower surface (20-I-5) and reddish (7-J-8 Domingo Red) on the upper petiole surface and on and in the petiole groove. The petiole is moderately pubescent on the upper surfaces and on the petiole groove ridges. The petiole is less pubescent to nearly glabrous on its under side. Glands:

From one to three large glands are usually present on the petiole stalk, usually from 3 to 11 mm below the juncture of the lower leaf blade and the petiole. Very occasionally one additional gland may be present on the basal portion of the leaf blade itself. Gland form is variable from globose to weakly reniform. Gland position is alternate and gland color is a reddish-maroon (7-J-9 Tanagra Red). Stipules: Stipules are medium in size, from 6 to 12 mm in length. Stipule form is linear lanceolate with narrowly serrate margins. Stipule color is a light green (21-K-2), often with a reddish tinge, especially along the stipule margins.

5. *Flower.*—Floral buds: Dormant buds are medium to large in size and dark brown in color (7-J-11 Cordova Brown). Bud form is conic and plump, and the buds extend nearly free from the bearing stem or spur. Bud surfaces are essentially glabrous. The buds are hardy under typical San Joaquin Valley climatic conditions. Bloom timing:

The bloom is moderately early in relation to the common cherry cultivar "Bing". Date of full bloom for the subject variety was Mar. 23rd in 1994. Size: The flowers are medium in size with a fully expanded diameter ranging from 33 to 39 mm. Bloom abundance:

The bloom quantity is abundant. From 2 to 3 flower buds can be present per node, most frequently 3. Petal size:

The petals are from medium to large in size, with a range of 17 to 21 mm in length and 14 to 16 mm in width. Petal form:

Petal form is most frequently obovate. Petal number is 5. Petal color:

Color of the petals is white (1-A-1). Petal claw form:

The petal claw is small in size, tapered and truncate in form. The claw is from 1.0 to 1.5 mm in length and averages 1.0 mm to slightly less in width. Petal margins:

The petal margins are undulate, especially apically. The petal apex is irregular but most frequently rounded in form. Pedicel:

Pedicel size ranges from 22 to 32 mm in length and averages 1.0 mm in thickness. The pedicel surface is glabrous. Pedicel color is a light green (18-I-3). Calyx and sepals:

Calyx color is a pale green (18-I-3) with darker and regular striations (18-J-5). The calyx surface is glabrous. Sepal color is a medium green (18-J-5). The sepals are average in size and ovate in form. The sepals surfaces are glabrous. Floral nectaries:

The nectaries are light green-yellow in color (18-L-4). The nectary color becomes slightly lighter in color with age. Anthers and stamens:

The flower anthers are average in size. Anther color is a bright yellow (9-K-2 Chrome Lemon) both ventrally and dorsally. Pollen in the anthers is abundant. Pollen color is a yellow-gold (9-L-3). The flower stamens are variable in length, with filaments ranging from 5 to 13 mm in length. Filament color is white (1-A-1). The longer stamens are somewhat longer than the pistil. Pistil:

Pistil length varies from 10 to 12 mm, including the ovary. Pistil color is a light green (19-L-2 Javel Green). The surface of the pistil is glabrous.

6. Fruit.—Production:

The new variety produces fruit on a regular basis. Excessive rainfall in 1995 (California) diminished average production by about 10%. Other year' production remained relatively stable in similar type growing conditions (weather). Maturity: The fruit is described as firm ripe at full commercial maturity. Date of first pick was Apr. 20, 1994 and the last pick date was Apr. 25, 1994. Size:

The fruit is medium to large in size with good uniformity. Cheek diameter ranges from 24.0 to 27.5 mm, suture diameter from 18.5 to 22.0 mm and axial diameter from 20.0 to 23.5 mm. Form:

Viewed from the suture aspect, fruit form varies from broadly ovate to somewhat oblate. From an apical aspect, fruit form is generally oval but somewhat constricted at both the ventral and dorsal suture lines, presenting a bi-hemispherical outline. Fruit symmetry is variable with both symmetrical and unsymmetrical fruit present. Suture:

The ventral suture line is narrow and inconspicuous, and extends from base to apex. The suture usually expresses the same coloration as the surrounding skin areas. The suture is often somewhat clefted over the basal shoulder, from 5 to 8 mm down from the stem attachment. The suture line is somewhat depressed on the ventral suture as it nears the apex. The dorsal side of the fruit is also somewhat depressed at the apex, and at times extending to the base, dorsally. Ventral surface:

The ventral surface is relatively smooth, with only a slight amount of low lipping. Stem cavity:

The stem cavity is small. Cavity width ranges from 10 to 11 mm, and cavity length from 8 to 9 mm. Cavity depth ranges from 4 to 5 mm. Cavity form is oval. Base:

The base is rounded and almost always oblique to the fruit axis, shorter on the ventral suture side. Apex:

The fruit apex is usually depressed, with a small calloused pistil point that is apical in position and usually located in the center of the apical depression. Stem:

The stem in general is medium in length varying from 32 to 49 mm. Stem thickness ranges from 1.5 to 2.0 mm at the center of the stem but is slightly thicker at the point of attachment to the base of the fruit (3.5 to 4.0 mm). The stem surface is essentially glabrous. Stem color is a medium green (20-K-5- Verdant Green). Skin:

The skin is of average thickness with a glabrous surface, is of medium acidity, and is tenacious to the flesh at commercial maturity. Skin color:

The skin is a bright glossy red, quite uniform throughout the skin surface, varying from a bright red at commercial maturity (3-L-12) advancing to a darker burgundy red at highest maturity (7-L-5 Algerian Red). Very few dots or russet spots are present. No ground color is visible at commercial maturity. Flesh color:

General flesh color is pink to reddish (3-G-10 Ember Glow) to (6-K-11 Cauldron Red) depending on maturity. Numerous light colored, tender fibers are present throughout the flesh. The color of the surface of the stone cavity is usually in the darker red range. Flesh texture:

The flesh is moderately firm with a slightly fibrous texture. Ripening:

The fruit ripens evenly. Flavor:

The fruit flavor is mild, slightly acidic with moderate to good sugar content, resulting in good overall flavor balance. Aroma:

Aroma is absent to very slight. Eating quality:

Good, especially considering the early season of maturity.

7. *Stone.*—Attachment:

Semi-freestone. The stone is nearly free laterally and along the dorsal suture. Some flesh and fibers usually cling to the stone along the ventral suture. Size:

Generally small in size. Stone length ranges from 10 to 11 mm, stone width from 8 to 10 mm and stone thickness from 6.5 to 7.0 mm. Fibers: Numerous short, light colored fibers present, attached along the ventral suture surface. Form: The stone form is variable but most frequently ovate. Base: The base is generally rounded. The base angle is most frequently slightly oblique to the stone axis. Hilum: The hilum is small and a narrow oval in form. Apex: The apex is rounded with no tip. Sides: The stone sides vary from equal to nearly equal. Surface: The stone surface is relatively smooth laterally, with a few low ridges near the basal shoulders, especially over the ventral shoulder. Ventral edge: The ventral edge is relatively narrow and slightly eroded along the median ridge. The center ridge is paralleled by two outer ridges which converge apically and basally. The ventral edge is usually most prominent basally where a low keel is present. Dorsal edge: The dorsal edge features a narrow ridge extending from the stone apex to within 2 to 3 mm of the stone base. A very thin, tight groove or line is present along the center of the ridge. Color: Color of the dry stone is a cream color (9-D-2 Cream). Tendency To Split: No tendency to split has been observed.

E. Characteristics distinguishable from other varieties: The new Red Crystal cherry variety can be characterized as a very early maturing, dark red colored, sweet cherry suitable for use in local markets as well as for long distance shipping. The new variety has some similarities to the sweet cherry variety "Brooks" (U.S. Plant Pat. No. 6,676) but also has some substantial differences. The principal difference between the two varieties is the date of maturity. In 1994, the Red Crystal matured with first pick on Apr. 20th while, in the same area, the Brooks variety matured with first pick on May 7th. This would place the maturity of the Red Crystal approximately two weeks ahead of Brooks. Other differences that are readily apparent include a difference in fruit stem length, with the stem of the Brooks in general substantially shorter than that of the Red Crystal. Fruit color differences also exist. The Brooks cherry develops full fruit color late in the maturity process and often has adequate sugar for harvest when the fruit shoulders are still yellow. In contrast the Red Crystal develops full red color before peak flesh maturity has been achieved.

F. Source: The new variety was a chance seedling which occurred in a cultivated area (farm land in a farming region) at applicant's 78 acre farm located at 10461 S. Buttonwillow Avenue, Reedley, Calif.

G. Breeding: Red Crystal was developed in 1988 by the inventor from the chance seedling which was about 8 years old. He grafted budwood onto one year old "Colt" rootstock and existing Bing cherry tree. This asexual reproduction took place in a cultivated area on a 20 acre farm located at 798 S. Chestnut Avenue, Fresno, Calif.

Again in 1992, the new variety was asexually reproduced by ProTree Nursery in a cultivated area at its farm located at N.W. Sellers and Sunset Avenue, Brentwood, Calif. and was given the designation P-75.

Reproduction was both by budding and grafting from the parent limb and these trees are growing at the ProTree Nursery farm located as indicated above. These asexually reproduced trees are true to the type of the original tree in all distinguishing characteristics of early bearing fruit, good taste and color to establish that these claimed characteristics are stable. It is thus clear from observation of the fruit that distinguishing characteristics have been transmitted to the next generation.

H. Pollination: The new variety is self fertile.

I claim:

1. A new and distinct variety of cherry tree described and illustrated, particularly characterized by an earlier maturing dark red, sweet cherry fruit than Brooks variety.

* * * * *